United States Patent
Wood et al.

(10) Patent No.: US 6,782,167 B2
(45) Date of Patent: Aug. 24, 2004

(54) LIGHT BEAM SPLITTER

(75) Inventors: Leroy M. Wood, Buffalo, NY (US); William R. Potter, Grand Island, NY (US)

(73) Assignee: Health Research, Inc., Buffalo, NY (US)

( * ) Notice: Subject to any disclaimer, the term of this patent is extended or adjusted under 35 U.S.C. 154(b) by 24 days.

(21) Appl. No.: 10/145,554

(22) Filed: May 14, 2002

(65) Prior Publication Data

US 2003/0215186 A1 Nov. 20, 2003

(51) Int. Cl.[7] .............................. G02B 6/26; G02B 6/42
(52) U.S. Cl. .......................... 385/47; 385/27; 385/39; 385/47; 385/140; 359/629; 606/2; 606/11; 606/17
(58) Field of Search .............................. 385/27, 31, 33, 385/39, 47, 140; 606/2, 10, 11, 15–18; 359/618, 627, 629, 633

(56) References Cited

U.S. PATENT DOCUMENTS

| 5,671,317 A | | 9/1997 | Weishaupt et al. ........... 385/137 |
|---|---|---|---|
| 5,798,867 A | * | 8/1998 | Uchida et al. ............... 359/629 |
| 5,948,291 A | * | 9/1999 | Neylan et al. ......... 219/121.77 |
| 6,084,717 A | | 7/2000 | Wood et al. ................. 359/629 |

* cited by examiner

Primary Examiner—Akm Enayet Ullah
Assistant Examiner—Daniel Petkovsek
(74) Attorney, Agent, or Firm—Michael L. Dunn

(57) ABSTRACT

An apparatus that efficiently and accurately directs or splits a non-polarized light beam input from a fiber optic into one, two, four or eight output beams wherein the light beam input is passed through a collimator, the apparatus uses non-polarizing beam splitters and the output beams are coupled to fiber optics using a lens matched to divergence of the beam to direct the beam into the fiber optic and uses an iris diaphragm attenuator to adjust the energy of the output beam prior to its entry into the fiber optic.

27 Claims, 8 Drawing Sheets

LIGHT BEAM SPLITTER

BACKGROUND OF THE INVENTION

This invention relates to beam splitters and more particularly relates to splitting a beam from a fiber optic source to fiber optic receivers. The invention more particularly relates to such beam splitters having input beams that originate as the output from a source fiber optic where the split beams are suitable for being directed to a plurality of secondary fiber optics through fiber optic couplers and the use of beams from the secondary fiber optics for therapeutic treatment, such as photodynamic therapy where an undesirable area on a patient, e.g. a tumor, is exposed to a beam from a secondary fiber optic after absorption by the tumor of a photosensitizing agent such as a porphyrin derivative. More particularly photodynamic therapy is based upon accumulation in tumors of a photosensitizing drug that is activated by visible light to produce a locally cytotoxic agent. For example PHOTOFRIN®, a porphyrin derivative approved for clinical use in the United States, Canada, Europe, and Japan, is activated by 630 nm light. Typically, light emitted from a tunable laser is delivered to a lesion by an optical fiber.

A problem associated with photodynamic medical procedures, e.g. photodynamic therapy, is that often numerous areas on the same patient in fact require treatment. Time involved in setting up and individually treating each of the numerous areas by a single light beam source can be extensive often exceeding the useful life of injected photosensitizing compound. Further, sequential treatment results in high cost due to time involved for trained personnel and inefficient use of costly equipment as well as significant discomfort on the part of the patient. It is of course possible to provide multiple light beam, e.g. laser, generators so that multiple areas can be simultaneously treated. Unfortunately, however, the cost for providing multiple beam generators for a single patient treatment is prohibitive.

It is known that laser beams can be split by beam splitters that comprise a partially reflective and partially transparent surface so that an incident laser beam is partially reflected and partially transmitted so that the beam is effectively split into two parts. Unfortunately, there has been no way to practically, consistently or economically commercially manufacture such surfaces so that they all will reflect 50 percent of the beam energy and transmit 50 percent of the beam energy at the same particular incident angle (the angle of the beam to the surface that splits the beam energy in half).

The manufacture of a beam splitter apparatus for more than two output beams thus would have been very difficult since the manufacturing process would have to take the particular incident angle of each individual beam splitter into consideration which requires the calculation of numerous angles of reflection and resulting various alignments and does not permit the use of any kind of standardized set angle hardware within the apparatus. The assembly of such a multiple beam splitter thus would have been tedious, time consuming and unacceptably expensive.

It has thus not been possible to easily and inexpensively manufacture a beam splitter to form four or more output beams where the output beam energies are within ten percent of each other and certainly not within five percent or less of each other.

It has been recently found that a beam splitter for a laser beam source could be made that overcame the above problems, e.g. as described in U.S. Pat. No. 6,084,717; however, such a device was not suitable for splitting a beam from a fiber optic source. Laser beam sources, e.g. as used in the device described in U.S. Pat. No. 6,084,717, are polarized, of small diameter, e.g. less than a few a millimeters, and without significant divergence. Laser beams are however expensive to produce and difficult to direct in that the entire laser source must be moved. By contrast, an input beam from a fiber optic is unpolarized, usually larger in diameter than a laser beam and has much greater divergence. A fiber optic source has definite advantages in that the beam can be easily directed simply by moving the end of the fiber optic without moving the entire light producing apparatus. Unfortunately, since beams from a fiber optic source are unpolarized, polarization thus cannot be used to attenuate individual beams from a fiber optic source. Further, even if fiber optic beam sources were conceived to be possible for use in splitters, due to divergence of beams from fiber optics, lens arrangements for laser beam sources would be completely unsuitable for beams from fiber optic sources. For example, diameter, focal length, and spacing for lenses suitable for laser beams would be different than such parameters for beams from fiber optics. Known devices for splitting beams from a laser source are thus completely unsuitable for splitting light beams from a fiber optic source.

The beam from a multimode fiber optic source is non-polarized and highly divergent.

BRIEF DESCRIPTION OF THE INVENTION

Figure 1:
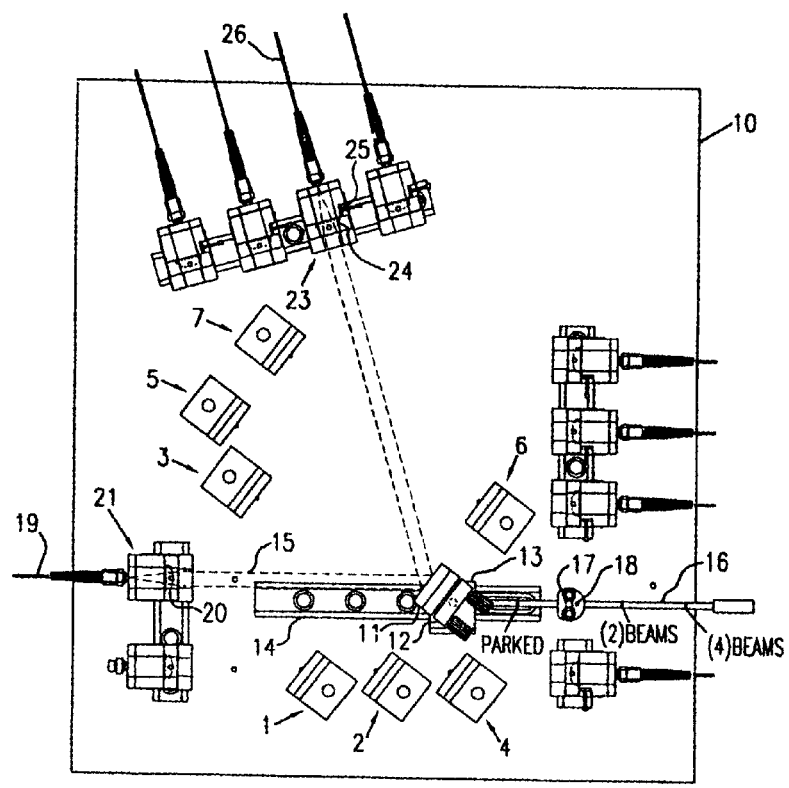
FIG. 1 shows a top view of an embodiment of the invention arranged to provide a single output beam.

In accordance with the invention an apparatus is therefore provided to efficiently and accurately split a light beam from a fiber optic input into eight outputs where the beam powers of the output beams are within ten and preferably within five percent of each other. More particularly, the invention comprises a light beam splitter apparatus capable of forming eight output beams from a single input from a fiber optic, where the apparatus has the following described structure.

Importantly, the input fiber optic coupler has a lens that collimates the beam from the fiber optic and the couplers to receive split beams have lenses suitable for receiving the split beams, i.e. they have the correct focal length and size. Especially important is that the couplers each have attenuators to adjust the strength of the beam as it enters the coupled fiber optic so that all exit fibers can be adjusted to emit beams of the same or different powers. Since the beams are not polarized, non-polarizing plate beam splitters are required. The Brewster window attenuators of the prior art will not function with unpolarized light. The invention therefore incorporates a variable iris located behind each coupler lens.

The apparatus includes an arrangement of seven beam splitters each of which splits an incident light beam from a fiber optic into two beams of approximately equal power at an identical incident angle for each splitter. The first splitter is one of the seven that has the ratio of reflected to transmitted power extremely close to unity(R/T=1) with a variance of less than about 0.5% at the common incidence angle. This choice is critical since a power imbalance produced at this splitter is propagated throughout the system. The second and third splitters are two that have R/T ratios very close to unity (a variance of less than about 1%) at the common incidence angle and are arranged so that the reflected and transmitted beams of the first splitter are directed to the second and third splitters. The second and third splitters each provide a reflected and transmitted beam when receiving an incident light beam.

The last four of the seven splitters can be those with R/T ratios different from unity at the common incidence angle but still close to unity (within a few percent and preferably within 1.5 percent). They are arranged so that the reflected and transmitted beams from the second and third splitters are directed to the fourth, fifth, sixth and seventh splitters at the common incident angle to provide their incident light beams. Each of the fourth, fifth, sixth and seventh splitters provide two light beams of nearly equal power when receiving an incident light beam to provide an apparatus output of at least eight beams.

An apparatus was constructed according to the above method of selecting beamsplitters. At the design wavelength of 630 nanometers the eight output beams powers had a standard deviation of ±3%. At 665 nanometers (the wavelength of a future photosensitizer) the standard deviation was 15%. This demonstrates the wavelength sensitivity of non-polarizing plate beamsplitters.

In a preferred embodiment of the invention, the apparatus further includes a second input beam collimator and an adjustable redirecting means for the beam input from the source fiber optic and redirecting it to selected splitters. The redirecting means may, for example, be adjusted to redirect the initial beam input from the source fiber optic away from all splitters to provide an apparatus output of a single beam. The redirecting means may also be adjusted for intercepting the initial beam input to redirect it toward one of the fourth, fifth, sixth and seventh splitters to provide an apparatus output of two beams or may be adjusted for intercepting said initial input to redirect it toward one of the second and third splitters to provide an apparatus output of four beams.

The redirecting means usually includes a repositionable mirror but may employ a prism rather than a mirror for redirecting the input beam. A mirror is usually preferred because it can usually redirect a beam with less energy loss than a prism. In a preferred embodiment, the redirecting means is a front surface mirror (called a fold mirror) having at least four adjustable positions wherein:

a) Position one intercepts the initial light beam input from a fiber optic to reflect the beam away from the splitters to provide a single light beam permitting a single apparatus output from an intercepting fiber optic coupler. Because of the flexibility of fiber optics, the fiber optic may simply be moved to a location so that its output impinges upon a mirror to reflect it to a single fiber optic output from the apparatus.

b) Position two intercepts the initial light beam input from a fiber optic to reflect it toward one of the sixth and seventh splitters to provide two light beams to provide two apparatus outputs.

c) Position three intercepts the initial light beam from a fiber optic to reflect it toward the third splitter to provide four beams permitting four apparatus outputs, and d) position four parks the fold mirror in a location that does not interfere with an eight beam output. Position four permits the input beam to strike the first splitter at the first splitter particular incident angle to provide eight apparatus outputs. Position four directs the input to the first splitter at the first splitter incident angle.

The energy of the apparatus output light beams is to be directed to and carried by fiber optics, thus fiber optic couplers are provided in paths of the apparatus output beams to receive the energy of such beams and for directing beam energy through a fiber optic. The use of such couplers provide an unexpected advantage in that the couplers provide a back reflection beam having an energy of from about 2 to about 6 percent, usually about 4 percent, of the energy received from an output beam. A means for aligning the output beams with the couplers can therefore be provided by varying the position of the couplers relative to an image formed by their back reflection beams.

The invention further includes a method for providing light beam treatment to a patient by simultaneously directing a plurality of light beams from fiber optics receiving energy from the apparatus of the invention to areas on a patient in need of light beam treatment. For example, the apparatus of the invention may be used as at least a part of a light delivery system for photodynamic therapy, e.g., in conjunction with fiber optic positioners as disclosed in U.S. Pat. No. 5,671,317.

DETAILED DESCRIPTION OF THE INVENTION

"Laser beam" as used herein means a single frequency coherent beam of light. "Light" means any electromagnetic radiation within the ultraviolet, visible and near infrared ranges.

"Beam" means light energy that travels in an essentially straight line direction in a vacuum subject to divergence.

"Light beam" as used herein means a beam of light that may be nearly coherent but is not as coherent as a laser beam.

"Splitter" means a device that divides a beam into two beams that travel in different directions. "Splitters" are usually partially transparent mirrors that reflect a part of the beam energy and transmit a part of the beam energy to form two beams.

"Incident light beam" means a beam that strikes a splitter at a particular incident angle and is the beam being split.

"Transmitted light beam" means the beam exiting a splitter.

"Reflected light beam" means the beam leaving the input surface so that the angle between it and the input beam is twice the angle of incidence.

"Beam Splitter apparatus" means an apparatus for splitting light beams that includes one or more splitters.

"Input beam" means a beam to be split that enters a beam splitter apparatus.

"Coupled beam" mean a beam coupled to a fiber optic.

"Output beam" means a beam after passing through a optical element such as a beamsplitter or a lens.

"Particular incident angle" means an angle of incidence to a surface of a beam splitter that will divide a beam striking the splitter at that angle into two beams having essentially equal energy.

The invention may be illustrated by reference to the following preferred embodiment.

A beam splitter apparatus or device was designed and constructed to split the output from a fiber optic into up to eight beams of essentially equal power, i.e., within about 10 percent of each other, preferably within about 5 percent of each other and most preferably within about 3 percent of each other. The power from each beam could be independently varied when necessary. The beam splitter device of this preferred embodiment is compact and of simple, low cost construction. Beam splitter mounts, collimators and fiberoptic coupler bodies were designed and fabricated specifically for the apparatus. Other components were obtained commercially and modified as required.

It has been found that the beam from a fiber optic cable with a 200 micron diameter core and a N.A.(Numerical Aperture) of 0.16 or less (beam divergence half-angle of 9.2 degrees or less) can be collimated, split into multiple beams and the energy in each beam focused into a spot only slightly larger than 200 microns. This energy can be efficiently input to treatment fibers having a core diameter of 400 microns or larger. The design concepts described in U.S. Pat. No. 6,084,717 are employed with such modifications as dictated by the nature of the light source. The beam splitting elements are non-polarizing and wavelength specific. The power of each split beam is set by an adjustable iris located behind the focusing lens. Two input beam collimators are used, one for the 8 beam output and one for the 4, 2, or 1 beam output(s). A modification is made to the method of terminating the 0.16 N.A. fiber optic cable with an SMA 905 connector. An insert aligns the 200 micron core of the source fiber with the longitudinal axis of the connector so that is approximately collinear with the optical axis of the apparatus. (The output of FDA approved lasers for photodynamic therapy is accessed through a SMA 905 connector port).

The beam splitter apparatus divides a beam from a fiber optic into up to eight beams of essentially equal power with negligible loss in total power. The device also allows four, two or one output(s), each of which may be coupled to an optical fiber for the delivery of therapeutic light to an individual treatment field. Means to control the power of the individual beams are provided, e.g. in the form of iris diaphragm attenuators, in order to equalize the treatment powers when optical fibers of different efficiencies were used, or when the treatment plan required dissimilar power outputs from each fiber. The apparatus is compact which is especially desirable because space is at a premium in clinics and laboratories.

The apparatus has eight fiber optic couplers and two fiber optic collimators. Each of these ten pieces are identical in construction and have a 12.7 mm diameter, 25.4 mm focal length plano-convex lens, with the exception that the bodies of the two collimators do not have a machined cavity to hold a variable iris.

The apparatus has seven plate beamsplitters acquired by the following selection process. Since the light source is not polarized, non-polarizing plate beam splitters are required. These are commercially available and designed to achieve at a specific wavelength a 50/50±5% split of the incident beam at a 45 degree angle of incidence with less than 0.5% power absorption. The ±5% tolerance is too great for a system in which each output beam is a result of three successive divisions. However these beamsplitters can be used at other than the designed angle of incidence to achieve a ratio of reflected power to transmitted power of unity (R/T=1) with negligible effect on the polarization and absorption properties. A commercially available 50 mm square by 3 mm thick plate beamsplitter designed for 632.8 nm works well enough at 630 nm. Three of these (preferably from the same manufactured lot) are cut into twelve 25 mm squares and each is measured for the incidence angle that produces a 50/50 split at 630 nm. The angle of incidence chosen for the apparatus is that for which one beamsplitter has an R/T ratio of unity, two have R/T ratios within 1% of unity and four of the remaining nine are selected that are the closest to a 50/50% split at that angle.

The optical components were mounted on a 14.4-inch by 13.5-inch by ½-inch aluminum jig plate which serves as an optical table 10. In FIG. 1 a one inch diameter plane mirror 11 is mounted on a mirror holder 12 fastened to a carrier 13 which translates on a microrail 14 parallel to the collimated beam 15. The mirror is set to the same angle of incidence as the seven splitters. A rod 16 passes through a centering block 17 and is attached to the carrier 13. A set screw with spring ball 18 in the centering block 17 engages one of four grooves in the rod 16 when the mirror 11 is at the desired location. The collimated input beam 15 is produced when the light from fiber optic source 19 passes through a collimating lens 20 mounted in the collimator 21. When the $1^{st}$ groove (closest to the handle of rod 16) is engaged mirror 11 intercepts the collimated input beam 15 to provide four beam outputs (FIG. 3). When the $2^{nd}$ groove is engaged two outputs are provided (FIG. 2) and when the $3^{rd}$ groove is engaged, one output is provided (FIG. 1). Eight beams (FIG. 4) are provided when the collimated input beam 15 is redirected by moving fiber optic source 19 to a second collimator 22 and the $4^{th}$ groove of rod 16 is engaged (parked position) so that mirror 13 intercepts no light beams.

As shown in FIG. 1, one output beam may be obtained. Fiber optic source 19 provides light beam 15 through collimating lens 20. Beam 15 is directed to mirror 11 when the $3^{rd}$ groove in rod 16 is engaged which reflects the beam to coupler 23. Lens 24 focuses the beam onto output fiber optic 26 through iris attenuator 25.

Figure 2:
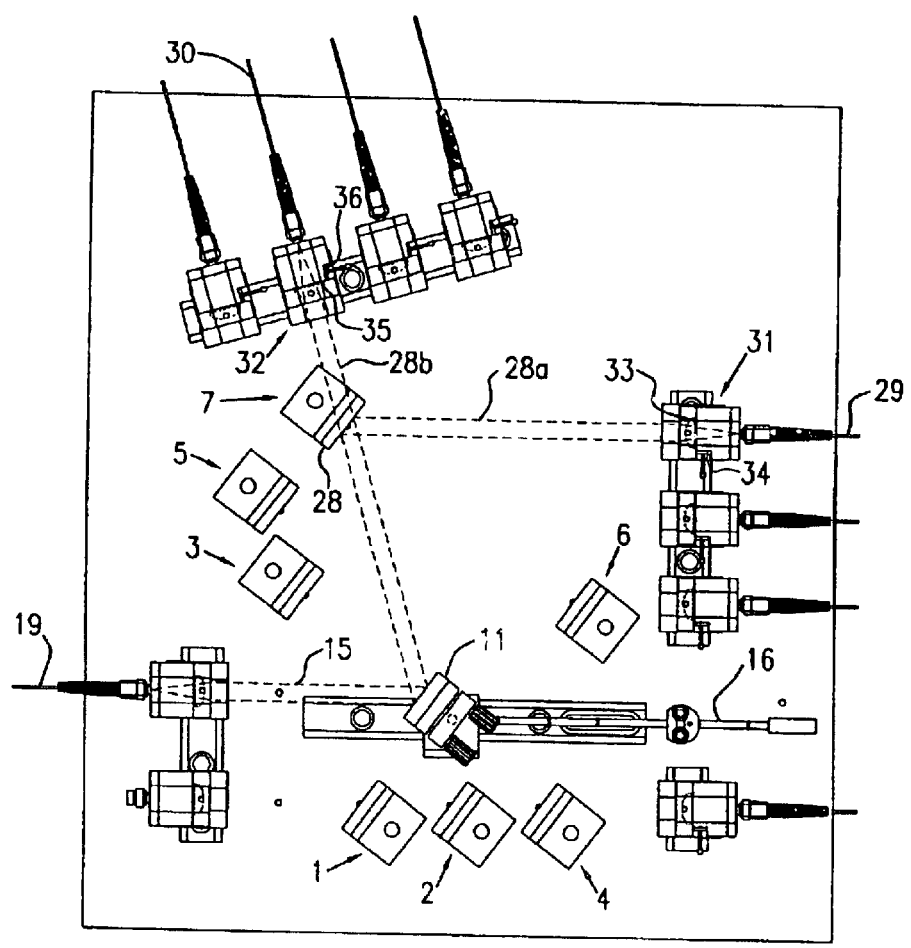
FIG. 2 shows a top view of an embodiment of the invention arranged to provide two output beams.
Figure 3:
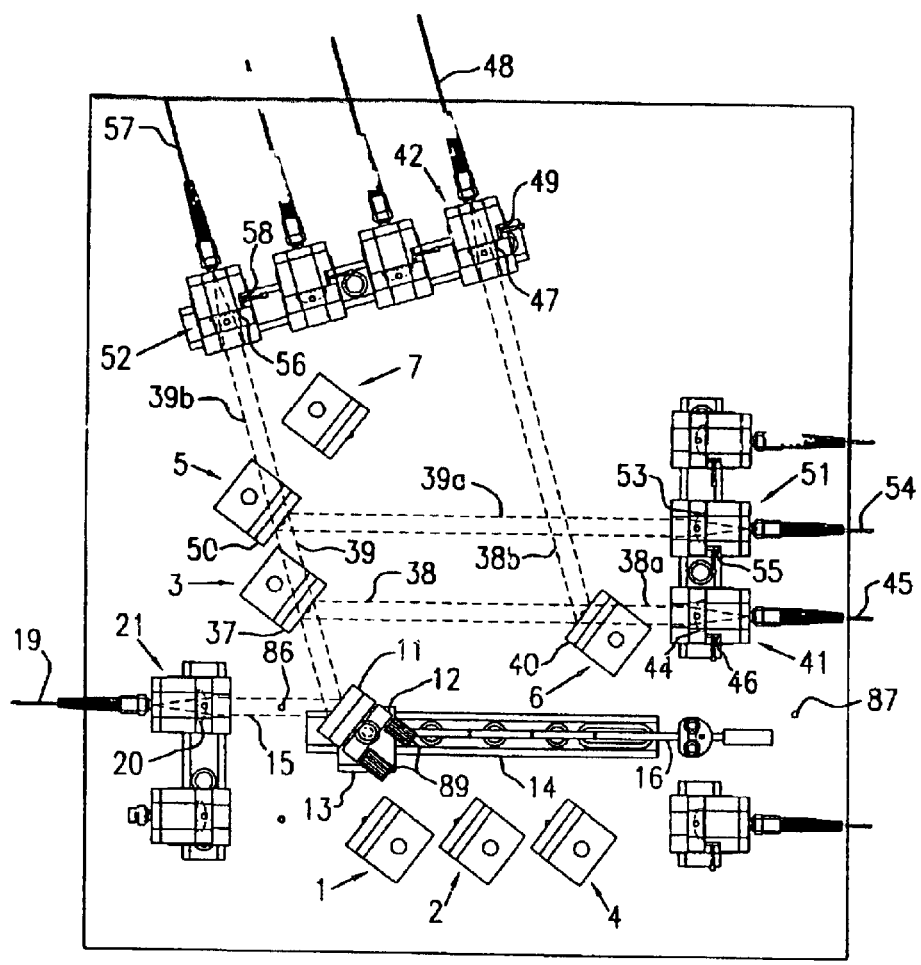
FIG. 3 shows a top view of an embodiment of the invention arranged to provide four output beams.

As best seen in FIG. 2, two output beams 27 and 28, respectively coupled to fiber optics 29 and 30, may be obtained. Input beam 15, from fiber optic source 19, as previously described, is reflected by mirror 11 to splitter 28 when the $2^{nd}$ groove in rod 16 is engaged. About half of the energy from the beam is reflected from splitter 28 to form beam 28a and the other half passes through splitter 28 to form beam 28b. Beams 28a and 28b are then coupled to fiber optics 29 and 30 respectively, through couplers 31 and 32 respectively. Lens 33 focuses beam 28a onto output fiber optic 29 through iris attenuator 34 and lens 35 focuses beam 28b onto output fiber optic 30 through iris attenuator 36.

As best seen in FIG. 3, four output beams coupled to fiber optics may be obtained. Beam 15 is reflected by mirror 11 to splitter 37 where it forms beams 38 and 39 when the 1st groove in rod 16 is engaged. Beam 38 is directed to splitter 40 to form beams 38a and 38b which are directed to couplers 41 and 42 respectively. Lens 44 focuses beam 38a onto output fiber optic 45 through iris attenuator 46 and lens 47 focuses beam 38b onto output fiber optic 48 through iris attenuator 49 as previously described. Beam 39 is directed to splitter 50 to form beams 39a and 39b which are in turn directed to couplers 51 and 52 respectively. Lens 53 focuses beam 39a onto output fiber optic 54 through iris attenuator 55 and lens 56 focuses beam 39b onto output fiber optic 57 through iris attenuator 58.

Figure 4:
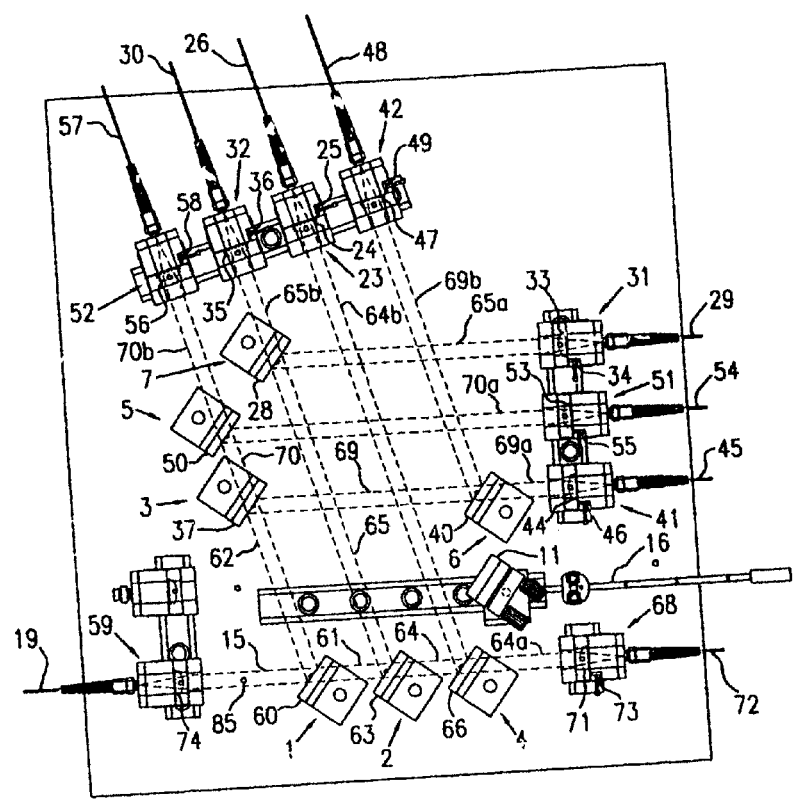
FIG. 4 shows a top view of an embodiment of the invention arranged to provide eight output beams.

As best seen in FIG. 4, eight beams can be formed by moving input fiber optic 19 to collimator 59 and mirror 11 to the parked position. Lens 74 in collimator 59 produces a collimated beam 15 which is directed to splitter 60 to form beams 61 and 62. Beam 61 is then directed to splitter 63 to form beams 64 and 65 each of which are again split by splitters 66 and 28 to form beams 64a, 64b, 65a and 65b which are directed to couplers 68, 23, 31 and 32 respectively. Similarly beam 62 is directed to splitter 37 to form beams 69 and 70 which are in turn directed to splitters 40 and 50 to form beams 69a, 69b, 70a and 70b which are directed to couplers 41, 42, 51 and 52 respectively. Lens 71 focuses beam 64a onto output fiber optic 72 through iris attenuator 73. The other seven output beams are coupled to their respective output fiber optics as previously described in FIGS. 1 to 3.

Figure 5:
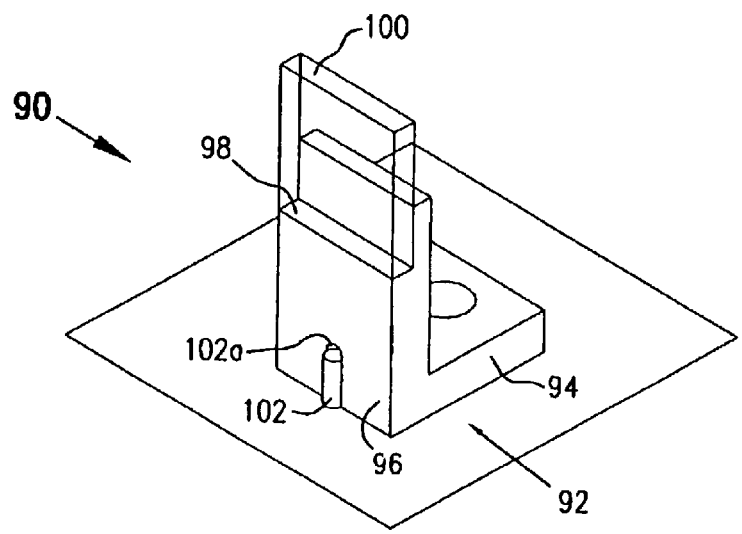
FIG. 5 is a perspective view of a preferred embodiment of a beam splitter and mount used in the invention.

The beam splitter apparatus of the preferred embodiment is shown in FIGS. 1–12. A preferred beamsplitter mount 90 is shown in FIG. 5. It is machined from 1-½ inch×1-½ inch×¼ inch thick bronze angle 92. It has a 1 inch square base 94 and a 1-¼ inch high front 96 into which a 3 millimeter deep shelf 98 is cut to hold a 3 millimeter thick beamsplitter 100. A ¹⁄₁₆ inch radius groove 102 is machined on center at the base of the mount. This groove accepts a ⅛ inch diameter dowel pin 102 which registers the position of the axis of rotation of the mount. When the incident beam is centered on the face of the beamsplitter and the mount is rotated about the dowel pin the reflected beam rotates without a lateral displacement. The mount is held in place with a ¼-20 bolt and bellville spring washer through a ⁵⁄₁₆ inch hole in the base of the mount.

Figure 6:
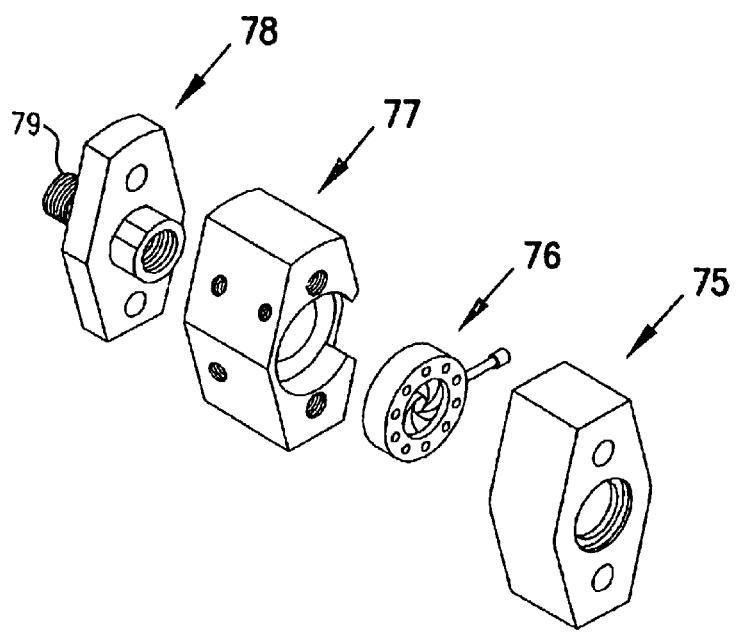
FIG. 6 is a perspective exploded view of a preferred embodiment of a fiber optic coupler for use in the invention. The figure also has two cross-sectional views relating to the alignment of treatment fibers to the output beams of the apparatus.
Figure 7:
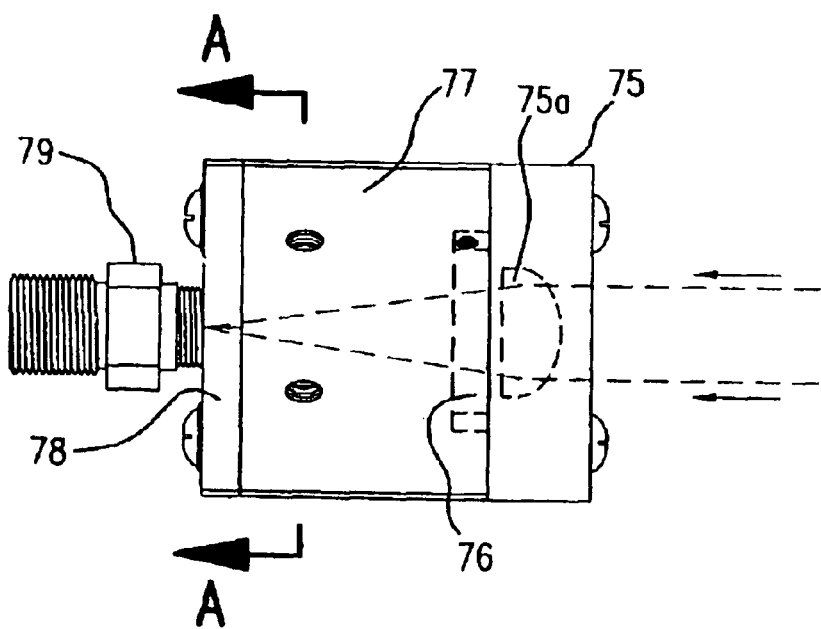
FIG. 7 shows a side view of the assembled optic coupler of FIG. 6.
Figure 8:
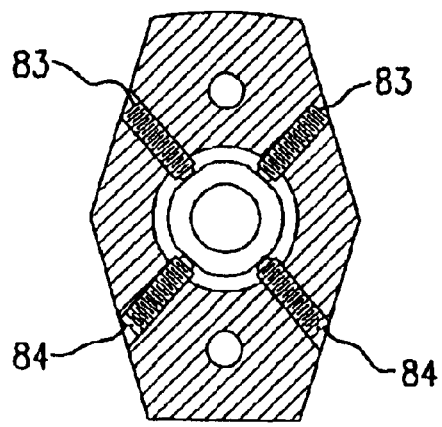
FIG. 8 shows a cross-sectional view of the coupler taken on lines A—A of FIG. 7.
Figure 9A:
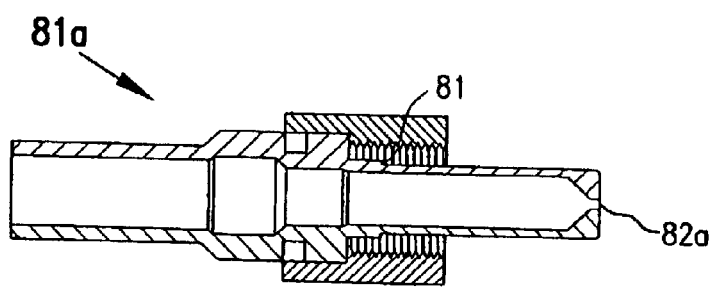
FIG. 9a shows a cross-sectional view of an SMA 905 multimode fiber coupler.
Figure 9B:
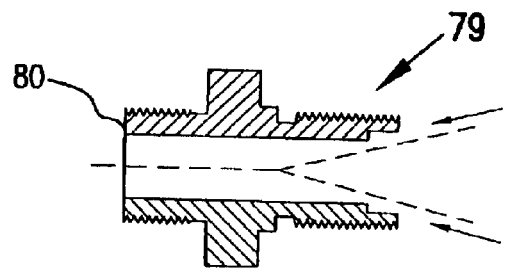
FIG. 9b shows a cross-section of an SMA sleeve holder for use in the invention.

The components of the coupler and a side view of the assembled coupler are shown in FIGS. 6 and 7. It consists of a commercial lens holder 75, a commercial iris 76, the coupler body 77 machined from brass, the fiber optic holder 78 also machined from brass and a modified commercial SMA to SMA mating sleeve connector 79 (shown in cross-section in FIG. 9b). The treatment fiber is threaded onto the mating sleeve. As shown in the cross-sectional view of the sleeve 79 the modification consists of an enlargement of the bore of the end of the sleeve 79 to prevent clipping the marginal rays of the focused beam (shown by the dotted lines with arrows). When the machined surface 80 at the opposite end of the sleeve 79 is in contact with reference surface 81 in an SMA 905 connector 81a (FIG. 9a) the output or input surface 82a of an optical fiber 82 is at a predetermined point within the sleeve. This point can be set in the focal plane of the lens in the collimators and couplers by using the source fiber set screws 83–84 at low power. A sharp magnified image of the fiber surface 82 is formed at infinity when the sleeve 79 is threaded into the fiber optic holder 78 so that the surface 82a is in the focal plane of the lens 75a. This position of the sleeve is secured with a lock nut (not shown). The surface 82a can be set on the optical axis of the lens 75a by adjusting set screws 83 against the ¾ pound end pressure exerted by a spring ball in the opposed set screws 84.

Figure 10:
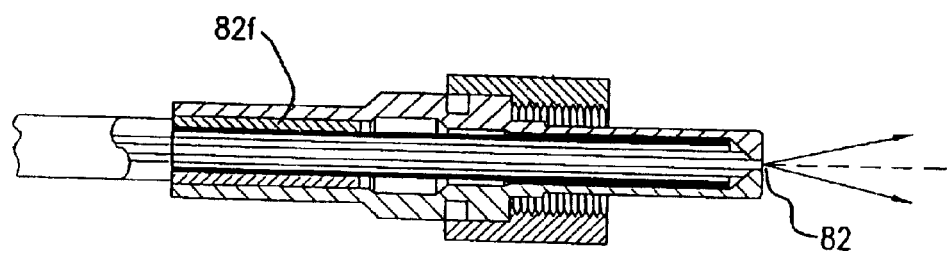
FIG. 10 shows a cross-sectional view of an assembled SMA 905 connector.
Figure 11A:
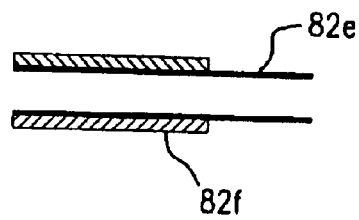
FIG. 11a shows a centering plug as assembled into the connector of FIG. 10.
Figure 11B:
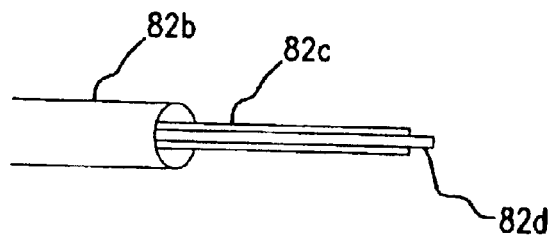
FIG. 11b shows a cladded and jacketed fiber optic assembled into the connector of FIG. 10.

SMA 905 connectors are not designed to produce an on-axis output beam (the hole in the ferrule has a low length to diameter ratio). An on-axis output beam as shown in FIG. 10 can be obtained with the following procedure. FIG. 11b shows the internal structure of a preferred silica/silica multimode 0.16 N.A. fiber 82, having a 3 mm jacket 82b. The fiber 82 is prepared for insertion into the SMA connector 81a by stripping a section of the 3 mm diameter jacket 82b exposing a 600 micron diameter buffered fiber 82c. The buffer is stripped from the tip of the fiber so that the 250 micron diameter cladded core 82d can fit through the hole in the ferrule of the connector 81a. FIG. 11a shows a cross-section of a 16 gauge hypodermic tubing 82e held in a centering plug 82f machined from brass. The hypodermic tube was reduced in diameter to the inside diameter of the ferrule and its length is the internal length of the SMA connector 81a. The plug is sized to slip inside the connector and holds the tube on center. The hypodermic tube and the plug are coated with epoxy and inserted into the connector. The stripped length of fiber is also coated with epoxy and inserted into the hypodermic tube as shown in FIG. 10. Standard procedures are followed in securing the connector to the cable jacket and polishing the surface of the fiber. The fiber optic source for the beamsplitter apparatus must have a N.A. of 0.16 or less and be terminated with an SMA connector as described above in order to efficiently transfer the source power to the treatment fibers.

A ray trace computer program was written in Visual Basic Language which calculated spot diagrams for every optical surface. It showed that all of the light emitted by a 200 micron diameter, 0.16 N.A. optical fiber could be split into eight collimated light beams which could be focused into eight spots of less than 300 micron diameter. The program calculated the position of 18 dowel pins marking the optical axis of the multiple beam segments. Seven pins located the position of the 7 beamsplitter mounts, 8 pins marked the 8 exit beams (these are not seen in FIGS. 1 to 4 as they are located under the output fibers), 1 pin, 85 in FIG. 4, located the center line of that collimated beam which produced 8 output beams and 2 pins, 86 and 87 in FIG. 3, marked the center line of the collimated beam used in the 4, 2, or 1 output beam(s) configuration. The program calculated the coordinates of the mounting holes for the 7 splitters and the 5 optical rails.

Figure 12:
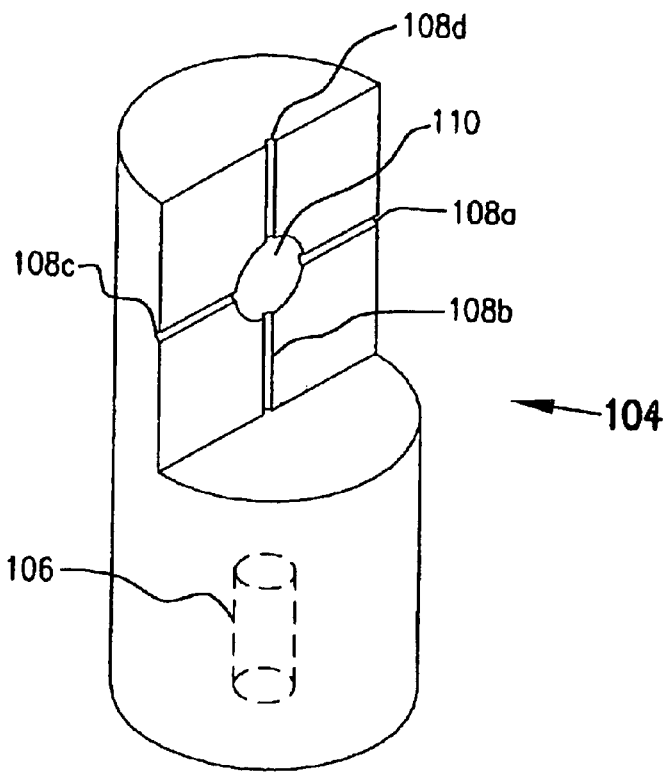
FIG. 12 is a perspective view of a tool used to align the optical elements of the apparatus.

FIG. 12 is a perspective drawing of a tool 104 used to align the optical elements of the apparatus. A dowel pin fits in a hole 106 (dotted lines) drilled in the base of the tool. Four orthogonal grooves 108a, 108b, 108c and 108d mark the center of a target hole 110 at the height of the optical axis. The hole is smaller than the collimated beam diameter. This makes it easy to visually center the beam on the target.

Alignment procedure for the beam splitter apparatus begins with all of the output fiber optic couplers and the fold mirror removed. The alignment tool is set on pin 85 (FIG. 4). The fiber optic source 19, set to emit a trace light beam, is connected to collimator 59 which is mounted on a carriage barely visible in the drawing. The carriage is slid onto a microrail to a position at which the trace beam is centered on the target hole in the tool. The tool is set on the pin that locates the output beam for fiber 72. The position of the light source in the focal plane of lens 74 is adjusted using set screws 83 and 84 (FIG. 8) so that the collimated beam passes through the unaligned beam splitters 60, 63 and 66 and is entered on the target. The target is moved back to pin 85 and the collimator is repositioned on the microrail, if required, to center the beam on the target. This procedure is repeated until the beam is on target at both pin locations. The position of collimator 59 is secured on the rail with a locking nut on the carriage.

Setting the angle of incidence on beam splitter 60 is the next step in the alignment. The tool is set on the pin that locates the output beam for fiber 57. The mount of beamsplitter 60 is rotated so that the reflected beam 62 passes through beamsplitters 37 and 50 and is centered on the vertical groove in the tool. Plastic shims in increments 0.0005 inch thickness are placed under the front or back of the mount of beamsplitter 60 as required to center the collimated beam on the horizontal grooves on the target. A ¼-20 bolt through a Bellville spring washer and the oversize hole in the base of the beamsplitter mount fasten the mount to the jig plate. This establishes beam 70$b$ since the subsequent small adjustments in the angles of beamsplitters 37 and 50 required to set the reflected beams 69 and 70$a$ will not cause an appreciable lateral shift in the transmitted beam 70$b$. Next collimator 52 (minus the treatment fiber) is mounted on a carriage and positioned on the microrail so that beam 70$b$ on passing through lens 56, the open iris 58 and the SMA sleeve falls on the center of the target. Using the same procedure beamsplitters 63 and 37 and collimators 32 and 41 are aligned next with the tool set on the pins locating the output beams for fibers 30 and 45 respectively. Next beamsplitters 66 and 50 and collimators 23 and 51 are aligned using the tool placed on the pins locating the output beams for fibers 26 and 54 respectively. Finally beamsplitters 40 and 28 and collimators 42 and 31 are aligned using the tool placed on the pins locating the output beams for fibers 48 and 29 respectively.

When a light beam enters a coupler, light is reflected from the input face of the attached fiber and from the distal end of the fiber since neither end of the fiber core is antireflection coated. The light from the distal end travels back through the fiber toward the coupler lens. That light and the light reflected from the input face are collimated by the coupler lens and travel up stream toward the fiber optic source 19. The power in the reverse beam is reduced by 50% at each of the three beamsplitters encountered in the path toward the source 19. Each reverse beam forms three images at infinity of the fiber face, some at the left side of FIG. 4 and some at the bottom of the figure. These can be observed on cards placed along the edges. For example the reverse beam from fiber 57 forms a reflected image to the left side at beamsplitter 50, another reflected image to the same side at beamsplitter 37 and a transmitted image at the bottom side at beamsplitter 60. When the other seven couplers are blocked by closing their irises the images due to fiber 57 alone are observed. Fiber 57 can be moved about in the focal plane of lens 56 by the set screws 83 (FIG. 6). There is a striking change in the images when the focused beam moves off the metal face of the SMA ferrule onto the quartz core. It appears as though a thin circular film is being drawn across a dimly lit circle. The focused beam is centered on the core of the treatment fiber when the film is centered on this circle. Thus the reverse beams of light are used to align each treatment fiber.

The final alignment task is setting the fold mirror to the same angle of incidence as the beamsplitters. As shown in FIG. 3 the source fiber 19 is moved to collimator 21. The collimator is aligned in the same manner as collimator 59, FIG. 4, using the alignment tool at pins 86 and 87. The plane mirror 11, the mirror mount 12 and the carriage 13 are assembled and placed on the microrail 14. The grooved rod 16 is attached to the carriage. An approximate setting of the angle is made by turning the mount 12 on the carriage 13 and sliding the carriage on the rail so that the parallel edges of a card are in contact with the mirror face and the beamsplitter 37. The distance from the right edge of carriage 13 to each groove in the attached rod 16 was calculated from data provided by the ray trace computer program. The rod 16 is set in the 4 output beam position. The horizontal and vertical controls 89 on the mirror mount 12 are adjusted so that the two beams 39$b$, the result of two transmissions, and 38$b$, the result of three reflections, are on target when the alignment tool is set on the pins behind couplers 52 and 42. The apparatus is now aligned.

The main utility of the beam splitter apparatus of the invention is to convert what would otherwise be a laborious and time consuming procedure into an acceptable and practical treatment using a fiber optic input beam without the complexity of using a laser beam that is difficult to control and adjust. For example, photodynamic therapy for treatment of patients with numerous basal cell tumors of the skin as a result of a genetic defect (nevoid basal cell carcinoma syndrome) is highly effective and desired by these patients because of often superior cosmetic outcomes compared to surgical procedures. Because each tumor or site must be exposed to therapeutic light for approximately 24 min., the sequential treatment of 40–50 lesions (as commonly presented) is completely impractical. The ability to treat 8 such lesions or sites simultaneously by using the beam splitter and specially designed fiber positioners makes this a practical and acceptable procedure for these patients and others with a large number of skin lesions.

What is claimed is:

1. An improved light beam splitter apparatus capable of forming eight output beams from an initial beam input, said splitter comprising:

an arrangement of seven beam splitters each of which splits an incident beam into two exit beams of equal energy at a particular incident angle for each splitter, at least some of said particular incident angles being different from each other for the different splitters, said apparatus comprising a first of the seven splitters, having a first splitter particular incident angle, and being arranged for receiving said beam input at the first particular incident angle;

second and third of the seven splitters having second and third particular incident angles, and being arrangeable so that the exit beams of the first splitter are directed to the second and third splitters, as their incident beams at the first particular incident angle;

each of said second and third splitters providing two exit beams when receiving an incident beam;

fourth, fifth, sixth and seventh of the seven splitters, having fourth, fifth, sixth and seventh particular incident angles, and being arrangeable so that the exit beams from said second and third splitters are directed to said fourth, fifth, sixth and seventh splitters at the first particular incident angle as their incident beam;

each of said fourth, fifth, sixth and seventh splitters providing two exit beams when receiving an incident beam;

the second and third particular incident angles being closer to the first particular incident angle than the fourth, fifth, sixth and seventh particular incident angles, the variance in energy between the two exit beams of the first splitter being less that 1 percent; the variance in energy between the two exit beams of each of the second and third splitters being less than about 2 percent at an incident beam angle about equal to the first particular incident angle and the variance in energy between the two exit beams of each of the fourth, fifth, sixth, and seventh splitters being less than about 5 percent at an incident beam angle about equal to the first particular incident angle, said apparatus being capable of providing at least eight output beams varying in energy from each other by less than about 10 percent;

wherein the improvement comprises using a collimated non-polarized light beam output from a fiber optic as an initial input light beam and using non-polarizing beam splitters to split the beams.

2. The apparatus of claim 1 wherein the variance between the energies of the two exit beams of the first splitter is less than 0.5 percent and the variance between the two exit beams of each of the second and third splitters is less than 1 percent.

3. The apparatus of claim 1 wherein the variance in energy between the two exit beams of each of the first, second and third splitters is less than about 1 percent at an incident light beam angle about equal to the first particular incident angle and the variance in energy between the two exit beams of each of the fourth, fifth, sixth, and seventh splitters being less than about 5 percent at an incident light beam angle about equal to the first particular incident angle, said apparatus being capable of providing at least eight output beams varying in energy from each other by less than about 5 percent.

4. The apparatus of claim 1 wherein the variance in energy between the two exit beams of each of the first, second and third splitters is less than about 0.5 percent at an incident light beam angle about equal to the first particular incident angle and the variance in energy between the two exit beams of each of the fourth, fifth, sixth, and seventh splitters being less than about 1.5 percent at an incident light beam angle about equal to the first particular incident angle, said apparatus being capable of providing at least eight output beams varying in energy from each other by less than about 3 percent.

5. The apparatus of claim 1 wherein the apparatus further comprises an adjustable redirecting means for intercepting said light input and redirecting it away from said first splitter.

6. The apparatus of claim 5 wherein the redirecting means is adjusted to redirect the beam input away from all splitters to provide an apparatus output of a single beam.

7. The apparatus of claim 5 wherein the redirecting means is adjusted for intercepting said beam input and redirecting it toward one of the fourth, fifth, sixth and seventh splitters to provide an apparatus output of two beams.

8. The apparatus of claim 5 wherein the redirecting means is adjusted for intercepting said beam input and redirecting it toward one of the second and third splitters to provide an apparatus output of four beams.

9. The apparatus of claim 5 wherein the redirecting means comprises a mirror having at least four adjustable positions wherein:

a) position one intercepts the initial input beam to reflect the beam away from the splitters to provide an apparatus output of a single beam;

b) position two intercepts the initial input beam to reflect it toward one of the fourth, fifth, sixth, and seventh splitters to provide an apparatus output of two beams;

c) position three intercepts the initial input beam to reflect it toward one of the second and third splitters to provide an apparatus output of four beams; and d) position four permits the initial input beam to strike the first splitter at the first splitter particular incident angle to provide an apparatus output of eight beams.

10. The apparatus of claim 1 wherein fiber optic couplers are provided in paths of the apparatus output beams to receive the energy of such output beams and for directing beam energy through a fiber optic wherein the couplers are provided with a lens matched to the beam divergence for directing the output beam into the fiber optic and are proved with an iris diaphragm attenuator to vary the energy of the output beam before it enters the fiber optic.

11. The apparatus of claim 10 wherein said couplers provide a back reflection beam having an energy of from about 2 to about 6 percent of the energy received from an output beam.

12. The apparatus of claim 11 including means for aligning the output beams with the couplers by varying the position of said couplers relative to an image formed by their back reflection beams.

13. An apparatus that efficiently and accurately splits a non-polarized light beam input from a fiber optic into a number of beams selected from the group consisting of one, two, four and eight output beams comprising a collimator through which the light beam input is passed, a series of non-polarizing beam splitters for receiving the light beam input from the collimator and arrangeable for splitting the input beam into the one, two, four or eight output beams and fiber optic couplers for coupling output beams to fiber optics where the couplers include a lens matched to divergence of the beam to direct the beam into the fiber optic and uses an iris diaphragm attenuator to adjust the energy of the output beam prior to its entry into the fiber optic.

14. A method for providing treatment to a patient by simultaneously directing a plurality of beams from fiber optics receiving light energy from the apparatus of claim 1 to areas on a patient in need of light treatment.

15. A method for providing treatment to a patient by simultaneously directing a plurality of beams from fiber optics receiving light energy from the apparatus of claim 2 to areas on a patient in need of light treatment.

16. A method for providing treatment to a patient by simultaneously directing a plurality of beams from fiber optics receiving light energy from the apparatus of claim 3 to areas on a patient in need of light treatment.

17. A method for providing treatment to a patient by simultaneously directing a plurality of beams from fiber optics receiving light energy from the apparatus of claim 4 to areas on a patient in need of light treatment.

18. A method for providing treatment to a patient by simultaneously directing a plurality of beams from fiber optics receiving light energy from the apparatus of claim 5 to areas on a patient in need of light treatment.

19. A method for providing treatment to a patient by simultaneously directing a plurality of beams from fiber optics receiving light energy from the apparatus of claim 9 to areas on a patient in need of light treatment.

20. A method for providing treatment to a patient by simultaneously directing a plurality of beams from fiber optics receiving light energy from the apparatus of claim 10 to areas on a patient in need of light treatment.

21. A method for providing treatment to a patient by simultaneously directing a plurality of beams from fiber optics receiving light energy from the apparatus of claim 13 to areas on a patient in need of light treatment.

22. Use of the apparatus of claim 1 as at least a part of a light delivery system for photodynamic therapy.

23. Use of the apparatus of claim 2 as at least a part of a light delivery system for photodynamic therapy.

24. Use of the apparatus of claim 3 as at least a part of a light delivery system for photodynamic therapy.

25. Use of the apparatus of claim 5 as at least a part of a light delivery system for photodynamic therapy.

26. Use of the apparatus of claim 9 as at least a part of a light delivery system for photodynamic therapy.

27. Use of the apparatus of claim 10 as at least a part of a light delivery system for photodynamic therapy.

* * * * *

UNITED STATES PATENT AND TRADEMARK OFFICE
CERTIFICATE OF CORRECTION

PATENT NO.        : 6,782,167 B2                                                Page 1 of 1
APPLICATION NO.   : 10/145554
DATED             : August 24, 2004
INVENTOR(S)       : Leroy Wood and William Potter It is certified that error appears in the above-identified patent and that said Letters Patent is hereby corrected as shown below:

After the title "LIGHT BEAM SPLITTER", please insert the following first paragraph:

GOVERNMENT RIGHTS
This invention was made with United States government support under grant number NIH CA 55791 from the NIH. The United States Government has certain rights in this invention.

Signed and Sealed this

Third Day of April, 2007

JON W. DUDAS
*Director of the United States Patent and Trademark Office*